United States Patent
Steel et al.

(10) Patent No.: US 9,063,158 B2
(45) Date of Patent: Jun. 23, 2015

(54) MULTI-STREAM HIGH-PRESSURE LIQUID CHROMATOGRAPHY MODULE

(75) Inventors: Colin Steel, London (GB); Farah Shah, Northwood (GB); Sajinder Luthra, London (GB)

(73) Assignee: GE Healthcare Limited, Buckinghamshire (GB)

( * ) Notice: Subject to any disclaimer, the term of this patent is extended or adjusted under 35 U.S.C. 154(b) by 462 days.

(21) Appl. No.: 13/499,775

(22) PCT Filed: Oct. 8, 2010

(86) PCT No.: PCT/US2010/051944
§ 371 (c)(1),
(2), (4) Date: Apr. 2, 2012

(87) PCT Pub. No.: WO2011/044440
PCT Pub. Date: Apr. 14, 2011

(65) Prior Publication Data
US 2012/0193555 A1 Aug. 2, 2012

Related U.S. Application Data

(60) Provisional application No. 61/249,707, filed on Oct. 8, 2009.

(51) Int. Cl.
*G01N 21/88* (2006.01)
*G01N 30/74* (2006.01)
(Continued)

(52) U.S. Cl.
CPC ............. *G01N 30/74* (2013.01); *G01N 21/85* (2013.01); *G01N 21/05* (2013.01); *G01N 21/33* (2013.01);
(Continued)

(58) Field of Classification Search
CPC .............. G01N 21/85; G01N 21/8507; G01N 2021/8557
USPC .................. 250/573, 574, 575, 576; 210/110, 210/198.2, 634, 635, 656, 659
See application file for complete search history.

(56) References Cited

U.S. PATENT DOCUMENTS 4,364,263 A 12/1982 Sankoorikal et al.
6,461,515 B1 * 10/2002 Safir et al. ........................ 506/12
6,911,151 B1 6/2005 Muller-Kuhrt et al.

FOREIGN PATENT DOCUMENTS

CN 1680039 10/2005
CN 101340960 3/2011
(Continued)

OTHER PUBLICATIONS

Krasikova et al; "Synthesis Modules and Automation in F-18 Labeling". Ernst Schering Foundation Symposium Proceedings, vol. 64, Jan. 1, 2007, pp. 289-316.
PCT/US2010/051944 ISRWO Dated Mar. 24, 2011.
Mowery, R., et al., Analytical Instrumentation, issue 2 (1978) pp. 71-75.
(Continued)

*Primary Examiner* — Kevin Pyo

(57) ABSTRACT

An HPLC module utilizes a combination of compound-dedicated hardware providing line clearance between differing radiosynthesis and includes multiple compound-dedicated HPLC inject valves, each inject valve directing a fluid to a serially-connected HPLC column and UV flowcell so as to prevent cross-contamination between differing radiopharmaceutical syntheses. The module provides a disposable fluid path from each UV flowcell allowing for radioactive detection, fraction collection, formulation and final product dispensing. In this manner, a level of GMP compliance is achieved that is suitable for meeting the requirements of an MHRA approved site-license.

14 Claims, 5 Drawing Sheets

(51) Int. Cl.
*G01N 21/85* (2006.01)
*G01N 21/05* (2006.01)
*G01N 30/46* (2006.01)
*G01N 30/88* (2006.01)
*G21H 5/02* (2006.01)
*G01N 21/33* (2006.01)
*G01N 21/03* (2006.01)

(52) U.S. Cl.
CPC ............. *G01N 30/466* (2013.01); *G01N 30/88* (2013.01); *G01N 2021/0321* (2013.01); *G01N 2021/0357* (2013.01); *G01N 2030/746* (2013.01); *G01N 2030/8868* (2013.01); *G01N 2030/8881* (2013.01); *G21H 5/02* (2013.01); *G01N 2021/0346* (2013.01)

(56) References Cited

FOREIGN PATENT DOCUMENTS

| | | |
|---|---|---|
| EP | 1394539 | 5/2004 |
| JP | 60-115854 | 6/1985 |
| JP | 2001-208738 | 8/2001 |
| WO | 2004/040295 | 5/2004 |
| WO | 2005/011832 | 2/2005 |

OTHER PUBLICATIONS

Qun, G., et al., Analytical Instrumentation, issue 1 (1984) pp. 33-39.
Shen, Y., et al., Analytical Chemistry, vol. 73, issue 13 (2001) pp. 3011-3021.
Huber, J., et al., Journal of Chromatography, 83 (1973) pp. 267-277.
Search Report dated Oct. 30, 2013 issued on corresponding Chinese patent application No. 201080055322.6.

\* cited by examiner

Top

Front

Side

MULTI-STREAM HIGH-PRESSURE LIQUID CHROMATOGRAPHY MODULE

This application is a filing under 35 U.S.C. 371 of international application number PCT/US2010/051944, filed Oct. 8, 2010, which claims priority to U.S. application No. 61/249,707 filed Oct. 8, 2009, the entire disclosure of which is hereby incorporated by reference.

FIELD OF THE INVENTION

The present invention is directed to the field of chromatographic separation or purification. More specifically, the present invention is directed to chromatography equipment components.

BACKGROUND OF THE INVENTION

Positron emission tomography works by measuring the spatial distribution of a specific molecular imaging probe, a so-called PET-tracer, in the body of the patient. The tracer is injected in trace amounts into the patient and has the ability to specifically bind to tissue or be enriched in certain areas because of their specific involvement in biological processes. PET-tracers are used in cancer diagnosis and therapy control.

Typically, tracer production includes a first step of synthesizing a tracer, followed by a purification step via high-pressure liquid chromatography (HPLC), followed lastly by a dispensing step where either singe doses of the tracer are dispensed for injection, or a bulk dose for still further dispensement is conducted.

With the development of automated synthesis systems, such as FASTLab®, sold by GE Healthcare, a division of General Electric Company (Liege, BE), tracer synthesis is provided by a disposable cassette operated by a control system (called the synthesizer). The cassette includes the pump, conduits, valves, reagents, reaction chamber(s), filters et al., and is connected to a source of radioactive isotope. Under operation by the synthesizer, the cassette draws the isotope and processes the isotope so as to attach it to a tracer molecule. After the synthesis process, the labeled compound is dispensed, again under direction of the synthesizer, from the cassette for transport to an HPLC system for further purification. After undergoing HPLC, the purified tracer is delivered to a dispense system.

The synthesizer, cassette, HPLC system, and dispense system are located in a shielded hot cell. As the space available in a given hot cell is fixed, the more equipment required to synthesize labeled tracer compounds will affect the free space in the hot cell. Given that systems such as FASTLab can synthesize different tracers, multiple HPLC or dispense systems are needed to make production runs of subsequent tracers. Given the space limitations in the hot cells and the risk of exposure to residual radioactivity, as well as the need for GMP compliance, switching to these alternate HPLC systems can be time consuming, reducing throughput of multiple PET tracers.

Delivery of multiple $^{18}$F radiotracers from the radiosynthesis platform can be realised if used in conjunction with a GMP compliant multi-compound radioHPLC system. However, no suitable HPLC device currently exists.

There is therefore a need in the art for an HPLC system which can accommodate multiple tracers without requiring extensive operator intervention to connect to a synthesis device.

DETAILED DESCRIPTION OF THE PREFERRED EMBODIMENTS

Figure 1:
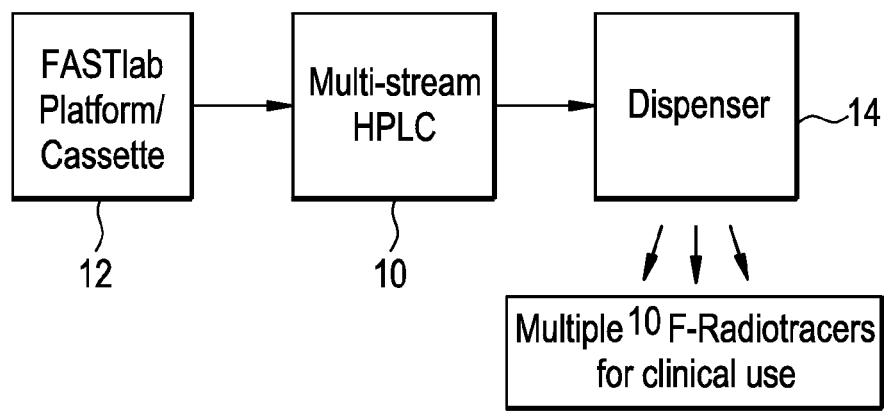
FIG. 1 depicts the production apparatus for a radioactive tracer incorporating a modular multi-stream HPLC system of the present invention.

The present invention provides a compact multi-stream radioHPLC module 10 with potential application to a radiosynthesis platform 12, such as the FASTLab® synthesizer sold by GE Healthcare, a division of General Electric Company (Liege, BE). With reference to FIG. 1, a GMP-compliant multi-compound radioHPLC module 10 enables multi-tracer synthesis from a single synthesizer 12. The output from HPLC module 10 may be provided to a dispense module 14 for dispensement of the purified radiotracer as required. Typically, the radiotracer is dispensed either into one or more dispense syringes or into a larger dispense vial for further dispensing at a point of use, such as a hospital or clinic.

A multi-stream radioHPLC system must not allow any cross-contamination between sequential purifications in order to meet a minimum level of GMP compliance. Ideally, such a system would be fully disposable (1), as per the cassette based concept of FASTLab. However, there are a significant number of technical challenges that need to be overcome in order to provide a fully disposable radioHPLC system. For example, system 10 includes a column select valve 18, which directs the output from synthesizer 12 to the compound dedicated hardware. Select valve 18 also selectably directs a wash/flush fluid therethrough, outputting to a sample collect vial so as to allow validation of line clearance within select valve 18.

HPLC module 10 enables delivery and purification of multiple $^{18}$F radiotracers from a single GMP hot-cell. Therefore, HPLC module 10 can accommodate both proprietary and non-propriety $^{18}$F-labeled imaging agents and thus would increase capacity and access to a wider portfolio of radiopharmaceuticals from a synthesizer platform. HPLC module 10 uses a validated gradient HPLC system to ensure correct delivery of eluent mixtures through the required HPLC columns. Radiotracers may be dispensed directly from radioHPLC module 10 (when operated within a GMP laboratory). HPLC module 10 is a compact device having a relatively small footprint for dispensing multiple radiotracers within the confines of a hot cell. The present invention is suitable for HIL GMP requirements, particularly for clinical research applications.

Figure 2:
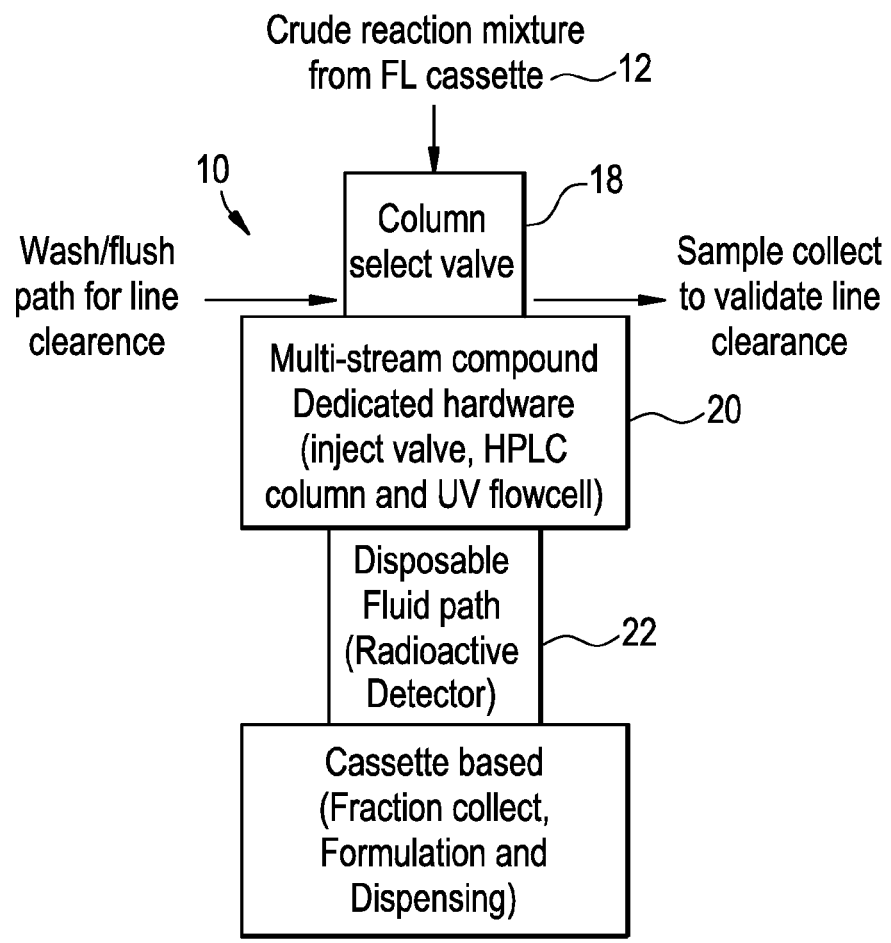
FIG. 2 depicts the overview of the multi-stream HPLC module of the present invention.

Referring now to FIG. 2, the present invention utilizes a combination of compound-dedicated hardware 20 providing line clearance between differing radiosyntheses. In this manner, a level of GMP compliance is achieved that is suitable for meeting the requirements of an MHRA approved site-license. HPLC system 10 includes multiple compound-dedicated HPLC inject valves 24, each inject valve 24 directing a fluid to a serially-connected HPLC column 26 and UV flowcell 28 so as to prevent cross-contamination between differing radiopharmaceutical syntheses. HPLC system 10 provides a disposable fluid path 22 from each UV flowcell for radioactive detection, fraction collection, formulation and final product dispensing. The dispense output from a radiosynthesis system, desirably from a FASTLab cassette or a cassette for another cassette-based synthesis system, is connected to the HPLC valves/columns via a multi-port valve, and although this valve is not essential to achieve the intended operation, it is retained to achieve a more robust level of automation through automatic column selection. Consequently, the common inlet to the valve introduces a small risk of cross contamination. Therefore, a wash/sample path is included in the design to enable validation of line clearance. While it is contemplated that formulation may take place downstream from both synthesizer 12 and HPLC module 10, it is further contemplated that fluid path 22 may provide the fluid back to synthesizer 12 for final formulation and ultimate dispensing to a dispense system. For example, HPLC module 10 may be arranged to re-direct the purified fluid back to the synthesis cassette for final formulation, and either the synthesis cassette or the HPLC module 10 will provide the valving (for the HPLC module, select valve 18 may be used) to direct the final formulation to a dispense system or dispense container.

Figure 3:
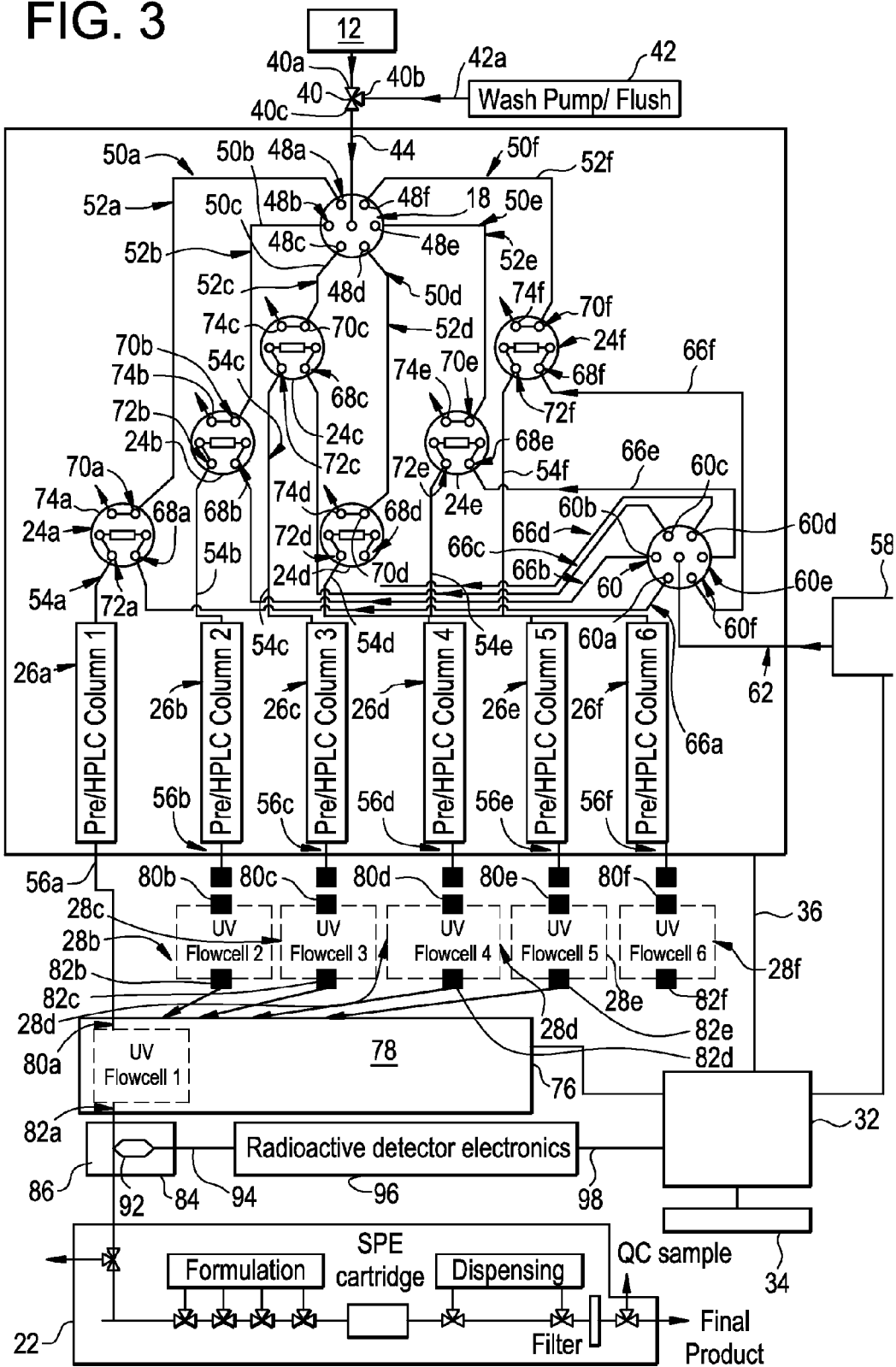
FIG. 3 depicts a schematic of a first multi-stream HPLC module of the present invention.

FIG. 3 provides a schematic diagram of HPLC system 10. The potential number of compounds that can be purified using the multi-stream system is determined by the selection of the multi-port valve (i.e. by the number of available ports) 18 and the hot cell space available for the module alongside the synthesizer itself. By way of illustration and not of limitation, FIG. 3 shows a six-column system as an example. Commercially available hardware can be utilized for the compound dedicated components 20 (inject valve 24, HPLC pre/main column 26 and UV flow-cell 28). The choice of UV detector is based upon the ease of flowcell interchangeability to enable compound dedicated flowcells to be utilized.

The remainder of the fluid path is cassette based. The transfer tube from UV flowcell 28 passes through a lead shielded radiodetector housing (the detector itself is not disposable) and connects to the cassette inlet valve. Ideally, the cassette utilizes FASTlab components. In the first instance, commercially available chemically inert (non-leaching) stopcock manifolds will be used. Standard solid phase formulation methods will be adopted and a disposable aseptic dispensing technique can be easily incorporated into the design (2), thus enabling injectable products to be delivered directly from the HPLC module. To achieve this function, the dispensing portion of the cassette should be supplied as a sterile pre-packaged assembly. A more preferable option would be to have the entire cassette provided as a sterile assembly.

As shown in FIG. 3, a planar base 30 supporting the valves, conduits, and columns of HPLC module 10. The optical flowcells 28 need not be supported on base 30. A control system 32 provides overall control and operation of HPLC module 10, including an interactive data display 34 for displaying system and operation status but also for receiving operator input for system operation. A generic control cable 36 is shown extending from control system 32 to base 30 to indicate that control system 32 directs the operation of the valves and columns of HPLC module 10.

HPLC module 10 includes a first source valve 40 providing selective communication between the output from synthesizer 12 and a wash fluid container 42 and select valve 18. Valve 40 includes first and second input ports 40a and 40b in fluid communication with the output from synthesizer 12 and fluid container 42, respectively. The present invention contemplates that output from synthesizer 12 may be either a separate container which holds the output from synthesizer 12 or an elongate conduit directly connected to synthesizer 12 so as to provide its output to valve 40 directly. Wash fluid container 42 holds a wash/flush fluid suitable for cleaning the conduits of the dedicated components 20 so as to render them GMP-compliant for handling the output of different synthesizer batches. An elongate conduit 42a conducts the wash fluid from container 42 to port 40b of valve 40. Valve 40 also operates under the control of control system 32 so as to direct either the synthesizer output fluid or the wash fluid therethrough and out outlet port 40c, through a delivery conduit 44 to an inlet port 46 of select valve 18.

Select valve 18 is operated by control system 32 and is configured to selectably direct fluid from inlet port 46 through one of outlet ports 48a-f. Each outlet port 48a-f is connected in fluid communication with a respective fixed fluid flowpath 50a-f. Fixed fluid flowpaths 50a-f respectively include an elongate first flow conduit 52a-f, an inject valve 24a-f, an elongate second flow conduit 54a-f, and an HPLC column 26a-f. An eluate conduit 56a-f extends from each respective HPLC column 26a-f to a respective optical, or ultraviolet (UV), flow cell 28a-f.

HPLC module 10 includes an HPLC pump 58, operated by control system 32, for selectably directing fluid through each fixed fluid flowpath 50 via its respective inject valve 24a-f on to its respective HPLC column 26a-f. HPLC module 10 provides a pump valve 60, also operated by control system 32, for directing the action of pump 58 to a selected one of inject valves 24a-f. Pressure conduit 62 extends between pump 58 to an inlet port 64 of pump valve 60. Pump valve 60 is configured to selectably direct a pumping fluid from pressure conduit 62 into input port 64, through valve 60, and out through one of the pump output ports 60a-f. HPLC module 10 provides an elongate pump conduit 66a-f extending between a respective output port 60a-f of valve 60 and pump inlet port 68a-f of inject valves 24a-f.

Each inject valve 24a-f further includes a fluid inlet port 70a-f, respectively, in fluid communication with conduit 52a-f, respectively. Each inject valve 24a-f further includes a fluid outlet port 72a-f, respectively, in fluid communication with second flow conduit 54a-f, respectively. Furthermore, each inject valve 24a-f includes a sample port 74a-f for directing wash fluid from container 42 to a sample or waste container (not shown). Wash fluid directed from container 42 and out one of sample ports 74a-f may be checked for quality control to ensure that conduits 52a-f, respectively, have been cleaned to GMP standards.

Each of optical flowcells 28a-f are disconnectably connected to eluate conduits 56a-f, respectively. When any of flowcells 28a-f are disconnected from their respective eluate conduits 56a-f, the present invention contemplates that the open ends of eluate conduits 56a-f will be capped so as to seal the conduit. Unused flowcells will also be capped at the connection ports for its respective eluate conduits. HPLC module 10 includes a flowcell housing 76 which receives each flowcell 28a-f being used. Flowcell housing 76 also incorporates a UV spectrometer detector 78 for interrogating fluid flowing through each flowcell. Detector 78 is operated by control system 32 which also reads and stores the data collected by detector 78. Each flowcell 28a-f thus includes an inlet port 80a-f for connection to a respective eluate conduit 56a-f and an outlet port 82a-f or connection to the disposable fluid path 22.

Figure 8:
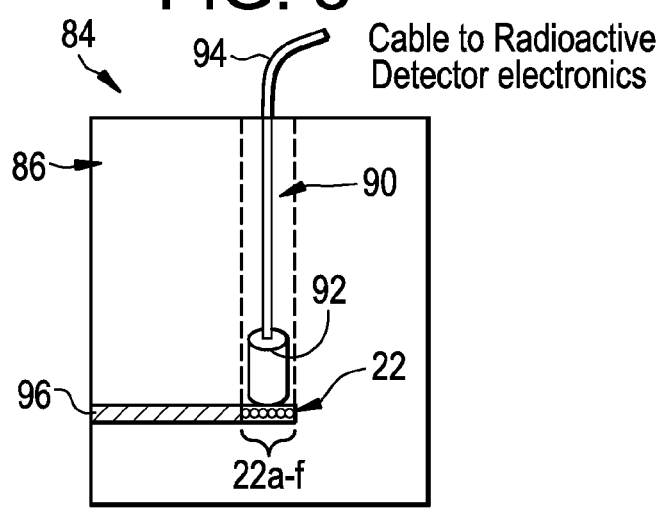
FIG. 8 depicts the assembled radioactive detector of the present invention.

HPLC module additionally includes a radioactivity detector 84 which detects the activity of the fluid flowing through the portion of disposable fluid path 22 leading from flowcells 28a-f. With additional reference to FIGS. 5-8, detector 84 includes a detector housing 86 which defines an open conduit cavity 88 extending therethrough. Detector housing 86 also defines an open interrogation channel 90 extending between a first end opening in fluid communication with conduit cavity 88 and a second end opening on the surface of housing 86. As shown in FIG. 8, elongate conduits 22a-f of disposable fluid path 22 are received within cavity 88 so that each of conduits 22a-f extend transversely across interrogation channel 90 such that channel 90 is in overlying registry therewith. Interrogation channel 90 accommodates a radioactivity detector instrument 92 therein for detecting the activity level of fluids flowing through any of conduits 22a-f. Instrument 92 is connected to radioactivity detector electronics 96 outside of housing 86 by a cable 94. Instrument 92 and detector electronics 96 are operated by control system 32 via an elongate cable 98 which also records the signal data therefrom. Housing 86 is desirably formed from a radiation shielding material such as lead. Housing 86 desirably incorporates a lead shim 96 into cavity 88 to both ensure proper positioning of conduits 22a-f in underlying registry with channel 90 and to provide additional shielding for operators.

Disposable fluid path 22 is contemplated to provide connection between the optical flowcells 24a-f and additional hardware which provides for additional formulation and/or dispensing of the fluid provided thereto by the fixed fluid path 20. It is therefore contemplated that fluid path 22 may direct the eluate fluid to a separate formulation cassette and/or a dispense cassette. In one embodiment, the present invention contemplates that fluid path 22 will re-direct the eluate to the synthesizer for final formulation of the eluate into a radiotracer. By way of illustration and not of limitation, the present invention contemplates that fluid path 22 will direct the eluate back to the synthesizer, such as a FASTLab cassette. Final dispense from the cassette will thus be directed to a dispense system. Desirably, the dispense system also incorporates a disposable cassette, such as that disclosed in commonly-assigned and co-pending patent application WO 2009/100428, with a priority filing date of Feb. 7, 2008, the entire contents of which are hereby incorporated by reference as if fully disclosed herein. Alternatively, or after such final formulation, the eluate may be considered to be the final radiotracer ready for dispensing by a disposable dispense cassette.

Figure 4:
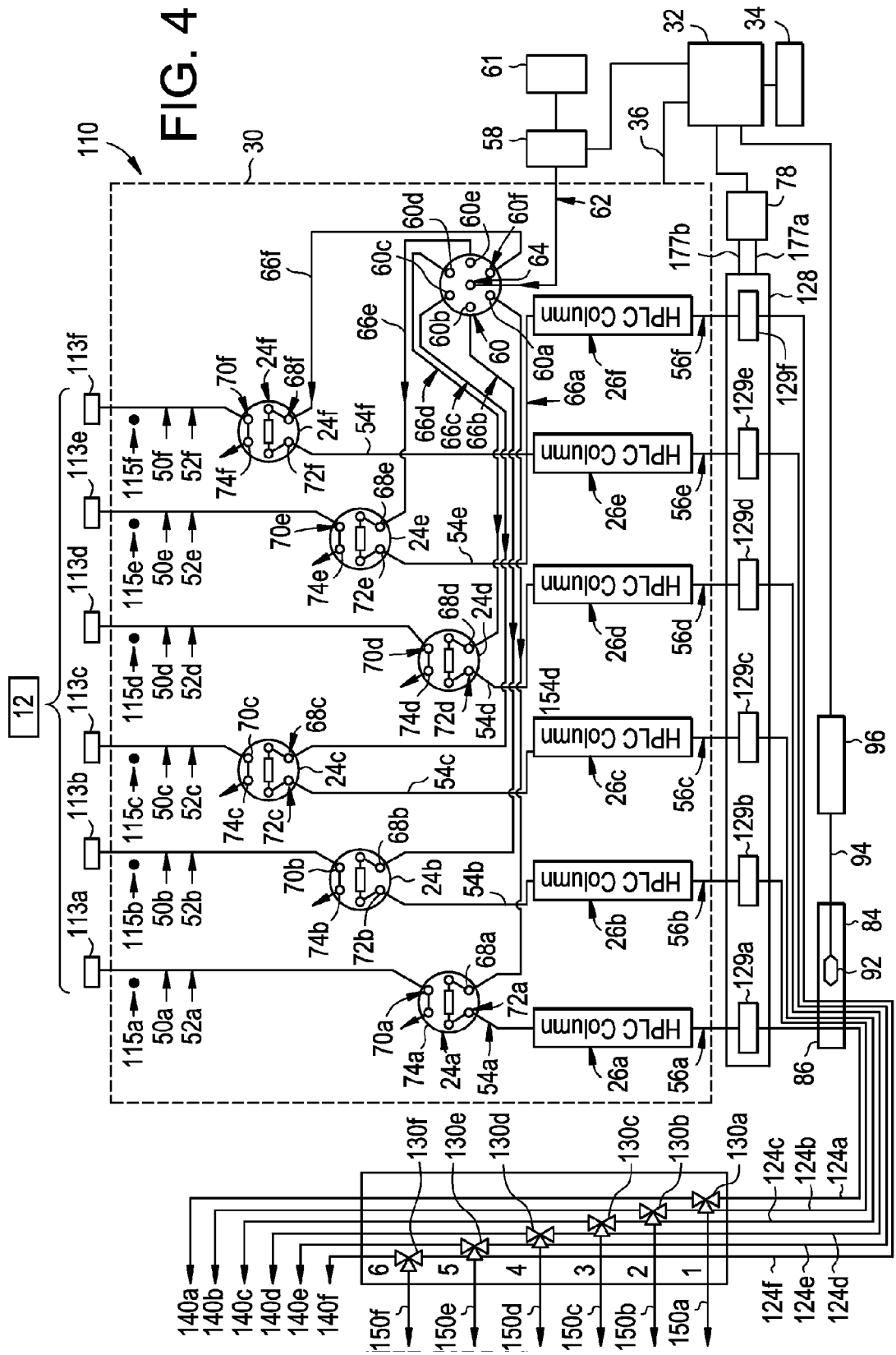
FIG. 4 depicts a schematic of a second multi-stream HPLC module of the present invention.
Figure 5:
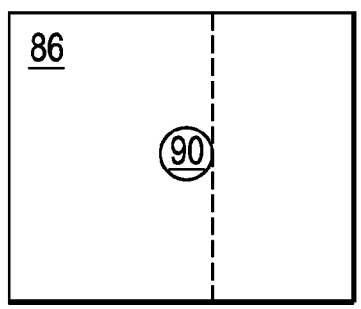
FIG. 5 depicts a front elevational view of a radioactivity detector housing of the present invention.
Figure 6:
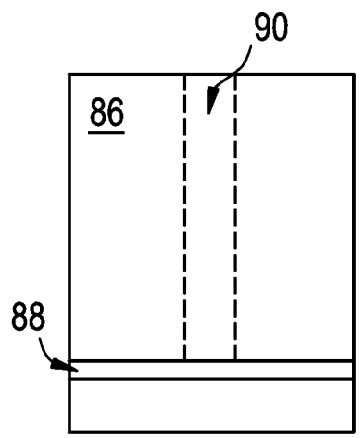
FIG. 6 depicts a side elevational view of the radioactivity detector housing of FIG. 5.
Figure 7:
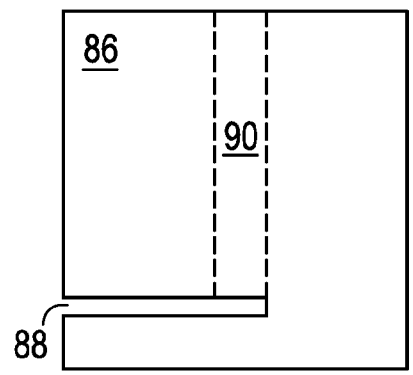
FIG. 7 depicts a top elevational view of the radioactivity detector housing of FIG. 5.

FIG. 4 depicts an alternate arrangement for an HPLC module 110 of the present invention. Module 110 incorporates many of the same components in a similar manner as described for module 10, and differences will be noted. Module 110 eliminates selector valve 18 from module 10, and instead employs direct connection between the individual flowpaths 50a-f to a synthesizer 10. Alternatively, the flowpaths 50a-f of module 110 may be connected to vial or container holding the product output from synthesizer 12. Each flowpath 50a-f terminates at a sealable connector 113a-f which provide for connection to a conduit extending to the output of synthesizer 12. Connectors 113a-f are sealable to be closed when not in use but otherwise open to conduct fluid therethrough. Each flowpath 50a-f has an associated indicator light 115a-f which will be lit by control system 32 to indicate which flowpath 50a-f is to be connected with synthesizer 12. Additionally, module 112 replaces the individual interrogation module s 28a-f with a multi-stream interrogation module 128, which includes individual interrogation flowcells 129a-f which are in dedicated connection to HPLC columns 26a-f, respectively, while employing only an optical interrogation cable and a signal receiving cable connected across interrogation module 128 so as to be able to interrogate each of the flowcells 129a-f with only a single detection beam. As only a single flow cell will be conducting an eluate therethrough at any given time, only a single interrogation beam is required, allowing the electronics for such to be positioned outside of the hot cell. Desirably, interrogation module 128 is provided as described in commonly-owned and co-pending patent application Ser. No. 13/499,757 entitled "Multi-Stream Spectrophotometer Module", filed at even date herewith, the entire contents of which are incorporated by reference as if fully described herein.

Additionally, FIG. 4 depicts that replaceable fluid path 22 of module 10 has a disposable fluid path 122 substituted therefore which provides individual fluid conduits 124a-f to extend from the output ports 182a-f of flow cells 129a-f, respectively. Each of fluid conduits 124a-f extend through a radiation detector housing 86 where the activity of any fluid being conducted thereby may be detected and measured by the radiation detecting equipment 96. Fluid path 122 further includes a bank of three-way valves 130a-f, each conducted to fluid conduits 124a-f, respectively, for directing the output fluid through a waste conduit 140a-f, respectively, or through a collection conduit 150a-f, respectively. Valves 130a-f are operable my control system 32 which will read the output from the UV interrogation equipment and radiation detection equipment to determine whether the fluid flowing through conduits 124a-f should be directed to a waste container connected to waste conduits 140a-f or through collection conduit 150a-f, respectively. As before, the present invention contemplates that collection conduits 150a-f may be connected to either a dispense container for receiving the final radiotracer product, or could be re-directed back to the appropriate synthesizer 12 for reformulation.

As further shown in FIG. 4, a planar base 30 supports the valves, conduits, and columns of HPLC module 110. The multi-stream optical interrogation module 128 need not be supported on base 30. Control system 32 provides overall control and operation of HPLC module 110, including an interactive data display 34 for displaying system and operation status but also for receiving operator input for system operation. A generic control cable 36 is shown extending from control system 32 to base 30 to indicate that control system 32 directs the operation of the valves and columns of HPLC module 110.

HPLC module 110 is connected to the output from synthesizer 12 such by a single fluid conduit 115 that connects to a respective fixed fluid flowpath 50a-f. Fixed fluid flowpaths 50a-f respectively include an elongate first flow conduit 52a-f, an inject valve 24a-f, an elongate second flow conduit 54a-f, and an HPLC column 26a-f. An eluate conduit 56a-f extends from each respective HPLC column 26a-f to a respective optical, or ultraviolet (UV), flow cell 129a-f of multi-stream interrogation unit 128.

HPLC module 110 includes an HPLC pump 58, operated by control system 32, for selectably directing fluid through each fixed fluid flowpath 50 via its respective inject valve 24a-f on to its respective HPLC column 26a-f. HPLC module 110 provides a pump valve 60, also operated by control system 32, for directing the action of pump 58 to a selected one of inject valves 24a-f. Pressure conduit 62 extends between pump 58 to an inlet port 64 of pump valve 60. Pump valve 60 is configured to selectably direct a pumping fluid from a reservoir 61 through pressure conduit 62 into input port 64, through valve 60, and out through one of the pump output ports 60a-f. HPLC module 110 provides an elongate pump conduit 66a-f extending between a respective output port 60a-f of valve 60 and pump inlet port 68a-f of inject valves 24a-f.

Each inject valve 24a-f further includes a fluid inlet port 70a-f, respectively, in fluid communication with conduit 52a-f, respectively. Each inject valve 24a-f further includes a fluid outlet port 72a-f, respectively, in fluid communication with second flow conduit 54a-f, respectively. Furthermore, each inject valve 24a-f includes a sample port 74a-f for directing wash fluid directed through conduit 52a-f, respectively, to a sample or waste container (not shown). Wash fluid directed out one of sample ports 74a-f may be checked for quality control to ensure that conduits 52a-f, respectively, have been cleaned to GMP standards.

Each of optical flowcells 129a-f are disconnectably connected to eluate conduits 56a-f, respectively. The present invention contemplates that each of flowcells 129a-f may remain connected to its respective eluate conduit 56a-f while not in use, as each flowcell 129a-f will be ready for use as needed. Although it is further contemplated that when any of flowcells 129a-f are disconnected from their respective eluate conduits 56a-f, the open ends of eluate conduits 56a-f will be capped so as to seal the conduit as will be the fluid ports on the unused flowcells. Interrogation module 128 is connected to a UV spectrometer detector 78 for interrogating fluid flowing through each flowcell. Detector 78 is operated by control system 32 which also reads and stores the data collected by detector 78. For simplicity, a single interrogation cable 177a extends between Interrogation module 128 and a single return signal cable 177b extends back from Interrogation module 128 to detector 78. Cables 177a and 177b are connected at opposite ends of interrogation module 128, as each of the flowchannels of flowcells 129a-f are coaxially-aligned and fluidically isolated by transmissive optical guides that allow a single interrogation beam from cable 177a to be detected by cable 177b, along with any signals returned with the beam shining on the eluate fluid flowing through module 128. Each flowcell 129a-f thus includes an inlet port 180a-f for connection to a respective eluate conduit 56a-f and an outlet port 182a-f for connection to the disposable fluid path 122.

HPLC module 110 additionally includes a radioactivity detector 84 which detects the activity of the fluid flowing through the portion of disposable fluid path 22 leading from flowcells 129a-f. Detector 84 operates as described for HPLC module 10.

Figure 9:
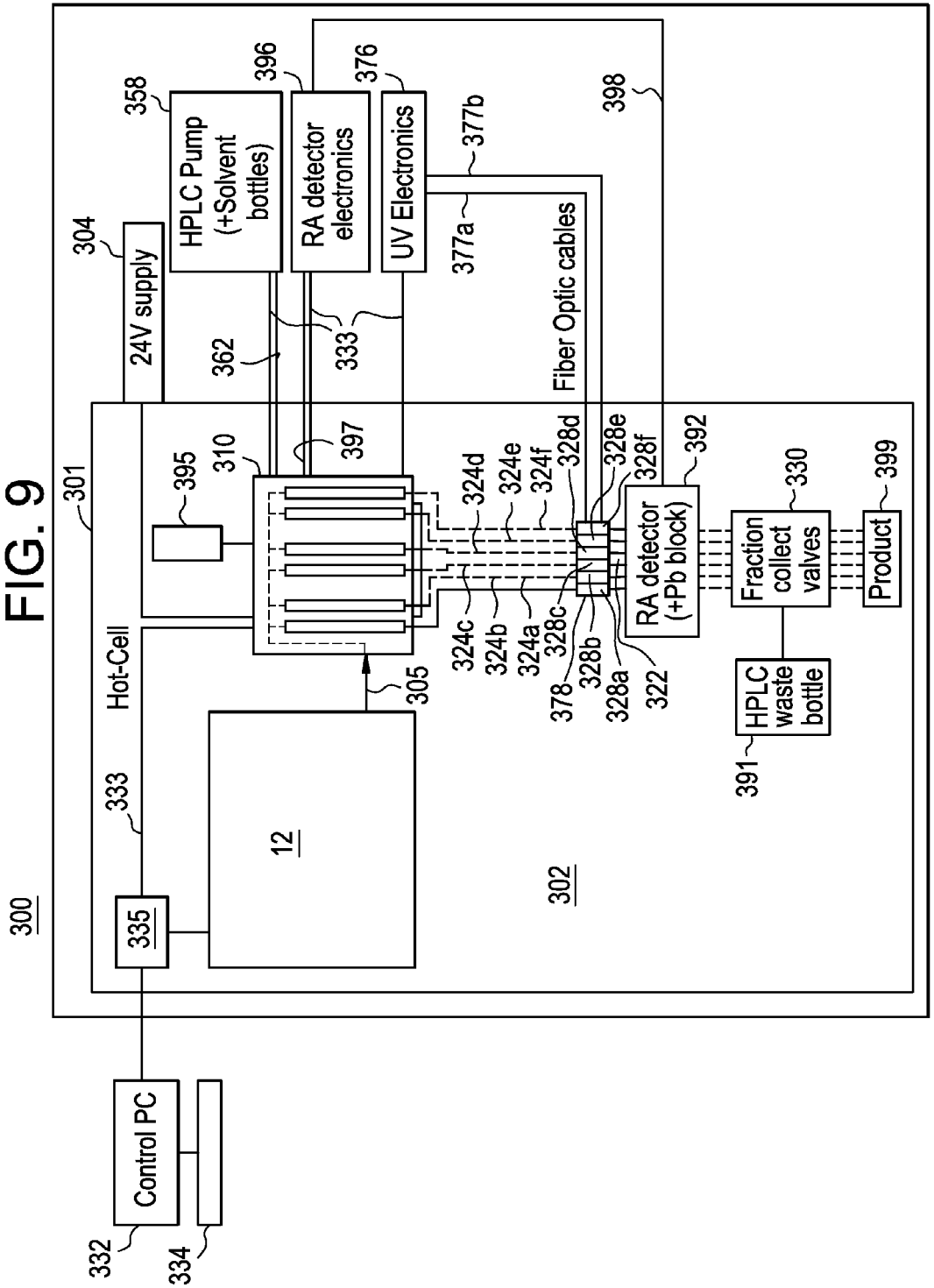
FIG. 9 depicts a schematic of the production apparatus of FIG. 1, showing the relative location of certain components with respect to a hot cell.

FIG. 9 depicts the arrangement of a radiosynthesis system 300 employing multi-stream HPLC modules 310 of the present invention. HPLC modules 310 are similar to either of modules 10 or 110 and will require an operator to connect the output line 305 from synthesizer 12 to HPLC module 310. System 300 includes components which are positioned either outside of a radiation-shielding hot cell 301 or within the hot cell cavity 302. A main power supply (not shown) outside of hot cell 301 powers the controller 332 and display 334 and synthesizer 12. A communications link 333 from an ethernet hub 335 directs the operation of HPLC module 310 and the equipment downstream from synthesizer 12. Communications link 339 from hub 335 directs the operation of synthesizer 12. Communications link 336 from controller 332 provides the signals to hub 335 for routing to the appropriate equipment. A local power supply 304, also located outside of hot cell 301, provides the power to the HPLC module 310 and equipment downstream from synthesizer 12.

HPLC pump 358, the radioactivity electronics 396, and photospectrometer electronics 376 for providing UV interrogation of fluid flowing through one of the flowcells 328a-f, are also located outside of hot cell 301. Pressure conduit 362 extends from pump 358 into hot cell cavity 302 to operate the inject valves of module 310 as directed by controller 332. Radioactivity electronics 396 receives signals over cable 398 from the radioactivity detector 392 located within cavity 302. Photospectrometer electronics 376 is connected to interrogation flow cell 378 via an interrogation cable 377a which provides the interrogation signal and via the return signal cable 377b which returns the signal from flow cell 378. Cables 377a and 377b are contemplated to be either single cables such as when using a multi-stream flow cell, eg, flow cell 128, or when individually connected to the single flow cell 328a-f through which the eluate fluid flows from the HPLC columns. Alternatively, cables 377a and 377b may each be bundled cables providing a dedicated interrogation and return cable connection to each of flow cells 328a-f. The fraction collect valve block 330 includes valves for each output fluid conduits 324a-f of fluid path 322 (similar to valves 130a-f of FIG. 4) for directing an radiotracer to a waste container 391 or to a product dispense vial 399. Only fluid conduit 324a is shown as a solid line to represent that only one of the fluid conduits of fluid path 322 is actively conducting eluate. HPLC pump 358, radioactivity electronics 396, photospectrometer electronics 376, and fraction collect valve block 330 are operated by controller 332 via communication link 333. Waste container 391 and product dispense vial 399 are shown as single containers to reflect that HPLC module 310 is dispensing through only a single conduit of flow path 322 so as to direct fluid to either a single waste container or a single dispense vial for each synthesis run. Similarly, only the active fluid conduits of flow fluid path 322 is shown as a solid line extending from the fraction collect valves to each of waste container 391 and product dispense vial 399. The present invention further contemplates that instead of dispensing to a product collection vial 399, a purified fluid may be directed back to synthesizer 12 for reformulation prior to final dispensing from synthesizer 12 either directly to either a product container or to a dispense system.

FIG. 9 also depicts a loop waste container 395 which collects either the samples or the waste directed through the sample/waste ports of the inject valves of the HPLC module 310. Additionally, radiation detector electronics 396 are connected via a cable 397 back to the HPLC module 310 so as to read the activity of fluid pumped from synthesizer 12 to the columns of module 310. Once activity is detected at HPLC module 310, controller 332 will know to direct the inject valves of HPLC module 310 to stop directing fluid to waste container 395 and to start directing fluid to the columns. Controller 332 may direct some of the radioactive fluid to the waste container 395 for sampling of the product prior to working by HPLC module 310.

The following describes an example operational procedure for the multi-stream HPLC module 10.

Set-Up:

Disposable fluid path 22 is installed on HPLC module 10. At least one of UV flowcell 28a-f for the required radiosynthesis is installed into UV detector housing 76. Each of the desired flowcell inlets 80a-f is connected to the appropriate HPLC column via the respective eluate conduit 56a-f, whilst the outlet 82a-f is connected to the disposable flow path 22. The required radioHPLC method is selected via control system 32 and eluent flow is established to equilibrate the column. Observation of the liquid flow to the appropriate waste reservoir can be used to verify that the correct fluid path 50a-f has been established.

Radiosynthesis:

An $^{18}$F radiotracer is prepared on a FASTlab cassette and transferred to the appropriate HPLC inject valve 24a-f via the column select valve 18. The reaction mixture is then passed onto the respective HPLC column 26a-f. The required fraction is collected. SPE formulation is performed using established methods (e.g. as exploited by GE Tracerlab FxFn and FxC platforms); for example, via elution from a C-18 Sep-Pak (sold by Waters, a division of Millipore) using EtOH/Saline solution. The formulated product is passed into the dispensing end of disposable fluid path 22. After use, the HPLC column and UV flowcell which were used are flushed with a suitable cleaning solvent. When safe to do so, the hot-cell can be re-entered to remove the UV flow cell for storage and to dispose of the spent FASTlab and disposable fluid path 22. The modules can then be set-up for a subsequent radiosyntheses. Due to the presence of $^{18}$F residues within the hardware, it is envisaged that clinical radiosynthesis can be performed daily. The frequency of operation may be increased through the use of secondary lead shielding and efficient wash/flush procedures.

Validation:

To achieve line-clearance between sequential radiosyntheses, there must be demonstration that no cross contamination has occurred between subsequent radiosyntheses. As each fixed fluid flowpath 20 is dedicated to a particular radioisotope, cross contamination is limited to occurring at inlet 46 of column select valve 18. After the HPLC column has been used and flushed with cleaning solvent, a sample aliquot of mobile phase can be passed through select valve 18 and collected at the relevant inject valve 24a-f. The aliquot can then be analysed for trace contamination. The process can be repeated for testing the next fluid path to be used. In this manner, a series of validated cleaning cycles can be established to demonstrate line clearance between syntheses. These tests can be repeated as required.

While the particular embodiment of the present invention has been shown and described, it will be obvious to those skilled in the art that changes and modifications may be made without departing from the teachings of the invention. For example, the HPLC modules of the present invention are scaleable to accommodate two or more separation columns. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. An high-pressure liquid chromatography ("HPLC") module comprising:
   a column select valve in for receiving a radioactive fluid to be purified;
   a plurality of fixed fluid flowpaths each in selectable fluid communication with an input port of said select valve, each said flowpath comprising an inject valve, an HPLC column, and an optical interrogation flowcells, in serial communication;
   a plurality of disposable fluid paths, each one of said plurality of disposable fluid paths serially-connected to the output of an individual one of said fixed fluid flowpaths such that each fixed fluid flowpath is in fluid communication with a respective one of said plurality of disposable fluid paths at the output of its respective optical flowcell;
   an HPLC pump;
   an HPLC pump valve configured to selectably direct pressure from said HPLC pump to one to said inject valves of said fixed flow paths;
   wherein said select valve is configured to selectably direct the radioactive fluid among said plurality of fixed flowpaths.

2. An HPLC module of claim 1, wherein each said fixed flow path further comprises
   an elongate first flow conduit extending between an output port of said select valve and its respective inject valve;
   an elongate second flow conduit extending between an output port of its respective said inject valve and its respective said HPLC column; and
   an elongate pump conduit extending between its respective inject valve and said HPLC pump valve.

3. An HPLC module of claim 1, wherein said HPLC pump valve further includes an input port in fluid communication with said HPLC pump and a plurality of output ports, such that each one of said output ports is in fluid communication with a respective one of said inject valves of said fixed flowpath, such that said HPLC pump valve selectably directs a driving pressure from said HPLC pump through one of its output ports to its respective one of said inject valves.

4. An HPLC module of claim 1, further comprising a source of wash fluid placed in selectable fluid communication with the input port of said select valve.

5. An HPLC module of claim 4, further comprising a flush sample receptacle placed in fluid communication with said source of wash fluid across said select valve.

6. An HPLC module of claim 5, wherein each said flush sample receptacle is placed in fluid selectable fluid communication with said source of wash fluid across its respective inject valve.

7. An HPLC module of claim 1, wherein each said optical flowcell is disconnectably connectable to its respective said HPLC column when not in use.

8. An HPLC module of claim 1, further comprising an optical flowcell housing for holding each said optical flowcell.

9. An high-pressure liquid chromatography ("HPLC") module of claim 1, further comprising a radiation detector housing defining an open detector cavity for receiving each said disposable flow path therethrough, said detector housing further defining an open interrogation channel in registry with said detector cavity, said housing positioning each said disposable flowpath in parallel transversely across said interrogation channel.

10. An HPLC module of claim 9, further comprising a radiation detector positioned within said interrogation channel so as to detect the level of radiation of a fluid flowing through one of said disposable flowpaths.

11. An HPLC module comprising:
    a plurality of fixed fluid flowpaths each connectable with to an output of a radiosynthesis device, each said flowpath comprising an inject valve, and a purification column;
    a plurality of optical interrogation flowcells, each of said plurality of optical interrogation flow cells in serial communication with a respective one of said fixed fluid flowpaths;
    a plurality of disposable fluid paths, each one of said plurality of disposable fluid paths serially-connected to the output of an individual one of said plurality of optical interrogation flow cells such that each fixed fluid flowpath is in fluid communication with a respective one of said plurality of disposable fluid paths at the output of its respective optical flowcell;

an HPLC pump; and an HPLC pump valve configured to selectably direct pressure from said HPLC pump to one to said inject valves of said fixed flow paths.

12. An HPLC module of claim 11, wherein said disposable fluid paths each comprise a fraction valve for selectable directing the eluate of an associated fixed fluid path to one of a waste reservoir and a fraction collection vial.

13. An HPLC module of claim 11, wherein said disposable fluid paths each comprise a fraction valve for selectable directing the eluate of an associated fixed fluid path to one of a waste reservoir and a reformulation system.

14. An HPLC module of claim 11, wherein said plurality of optical interrogation flowcells comprise a single interrogation module and are connected to a first and second fiber optic cable at opposed ends across said interrogation module, said first and second fiber optic cables able to interrogate an eluate flowing through any of the plurality optical interrogation flowcells of said interrogation module.

* * * * *